(12) United States Patent
Bodor et al.

(10) Patent No.: US 8,758,223 B1
(45) Date of Patent: Jun. 24, 2014

(54) TEST EQUIPMENT FOR ENDOSCOPES

(75) Inventors: Zoltan A. Bodor, Plantation, FL (US); Matthew T. Goodale, Davie, FL (US); Oscar Jerome Williams, Miramar, FL (US); Aurelian Marius Maris, Davie, FL (US)

(73) Assignee: Integrated Medical Systems International, Inc., Birmingham, AL (US)

( * ) Notice: Subject to any disclaimer, the term of this patent is extended or adjusted under 35 U.S.C. 154(b) by 1000 days.

(21) Appl. No.: 12/572,659

(22) Filed: Oct. 2, 2009

Related U.S. Application Data

(60) Provisional application No. 61/102,070, filed on Oct. 2, 2008.

(51) Int. Cl.
*A61B 1/00* (2006.01)
*A61B 1/06* (2006.01)
*G01N 21/00* (2006.01)

(52) U.S. Cl.
USPC ........... 600/101; 600/102; 600/127; 356/73.1

(58) Field of Classification Search
CPC .............................. A61B 1/00165; A61B 1/07
USPC ......... 600/101, 103, 108, 127, 160, 117, 109, 600/182, 188, 478; 356/244, 213, 124, 356/124.5, 125, 127, 73.1, 237.2; 348/65, 348/61, 68; 73/800
See application file for complete search history.

(56) References Cited

U.S. PATENT DOCUMENTS

| | | | | |
|---|---|---|---|---|
| 4,613,232 A * | 9/1986 | Diener et al. | .................. | 356/124 |
| 5,820,547 A * | 10/1998 | Strobl et al. | .................. | 600/127 |
| 5,879,289 A * | 3/1999 | Yarush et al. | .................. | 600/179 |
| 5,923,416 A * | 7/1999 | Rosow et al. | .............. | 356/124.5 |
| 5,953,112 A * | 9/1999 | Rosow et al. | ................. | 356/73.1 |
| 5,966,210 A * | 10/1999 | Rosow et al. | ................. | 356/213 |
| 6,069,691 A * | 5/2000 | Rosow et al. | .............. | 356/124.5 |
| 6,106,456 A * | 8/2000 | Storz | ............................ | 600/102 |
| 6,203,492 B1 | 3/2001 | Davis | | |
| 6,388,742 B1 * | 5/2002 | Duckett | ...................... | 356/73.1 |
| 6,498,642 B1 * | 12/2002 | Duckett | ........................ | 356/244 |
| 6,673,011 B1 * | 1/2004 | Hilger | .......................... | 600/117 |
| 6,833,912 B2 * | 12/2004 | Lei et al. | ....................... | 356/124 |
| 7,022,065 B2 * | 4/2006 | Leiner et al. | ................. | 600/101 |
| 7,349,083 B2 * | 3/2008 | Draggie et al. | ............ | 356/241.1 |
| 7,833,150 B2 * | 11/2010 | Yamamoto et al. | ........... | 600/102 |
| 8,040,496 B2 * | 10/2011 | Leiner et al. | ................. | 356/73.1 |
| 8,382,657 B1 * | 2/2013 | Bodor et al. | .................. | 600/101 |
| 2003/0100818 A1 * | 5/2003 | Lei et al. | ........................ | 600/117 |
| 2005/0049457 A1 * | 3/2005 | Leiner et al. | ................. | 600/117 |
| 2008/0228031 A1 * | 9/2008 | Leiner et al. | ................. | 600/109 |

* cited by examiner

*Primary Examiner* — John P Leubecker
*Assistant Examiner* — Ronald D Colque
(74) *Attorney, Agent, or Firm* — C. Brandon Browning; Maynard, Cooper & Gale, PC

(57) ABSTRACT

An endoscope testing apparatus including a base, a main rail coupled to the base, a first centering mount coupled to the main rail, an optical test target holder coupled to the main rail, a second centering mount coupled to the optical test holder, the second centering mount being coaxially alignable with the first centering mount, and an optical scanning device coupled to the main rail and coaxially alignable with the first centering mount and the second centering mount. The test target holder includes an optical test target having a selectively adjustable distance between the optical test target and the second centering mount and a selectively adjustable angle formed between an axis formed by the centering mounts and the test target.

30 Claims, 8 Drawing Sheets

TEST EQUIPMENT FOR ENDOSCOPES

RELATED APPLICATIONS

The present application claims priority to pending U.S. Provisional Patent Application No. 61/102,070, filed Oct. 2, 2008, and incorporates by reference the entirety thereof.

FIELD OF THE INVENTION

The present invention is directed to a device for testing optical equipment, and more particularly, to an endoscope testing device and method of using same.

BACKGROUND OF THE INVENTION

Technical and medical endoscopes are delicate optical instruments that are introduced into technical and human cavities for inspecting the interiors of such cavities. Endoscopes can be rigid endoscopes containing a lens system, flexible endoscopes containing a flexible image guiding bundle or video endoscopes. These endoscopes have a small diameter of a few millimeters but are often several hundreds of millimeter long.

Endoscopes generally comprise an outer tube and an inner tube. The space between the outer tube and the inner tube is filled with illumination fibers which guide externally created light inside of the cavities being inspected. Rigid endoscopes have inside the inner tube an optical system that relays images of a cavity from the distal tip of the endoscope back to the proximal end of the endoscope. This relayed image can be observed at the proximal end by the operator's eye, or a video camera can capture the image.

In use, rigid endoscopes are inserted along an insertion tube which cannot freely move in the body cavity. Thus, to look at a direction adjacent to the insertion direction of a rigid endoscope, the rigid endoscope often includes a deflecting prism at the distal tip of the optical system. In flexible endoscopes the image is relayed by a fiber image bundle to the ocular at the proximal end of the endoscope. Video endoscopes have a chip built into the distal tip of the endoscope that delivers the image in electronic form directly to an external video controller.

Because of their extreme physical dimensions, endoscopes are often stressed during cleaning, sterilization and usage. These stresses can cause bending of the instruments, or chipping, breaking or dislocating of the glass lenses or the deflection prisms. Further, the illumination fibers can break, debris can accumulate on the end of the fiber illumination bundle or on the windows enclosing the optical system, and fluid can enter the optical system of the instruments during cleaning or sterilization. Therefore, endoscopes are often damaged and their performance degraded to an extent where the safe usage of the instruments is no longer warranted. When this occurs, the damaged endoscopes must be separated form the inventory and properly cleaned or sent out to a service company for internal cleaning or repair. However, if a damaged endoscope is not detected prior to a planned surgery, the medical procedure can be delayed, canceled or the outcome of the procedure can be compromised.

In the patent literature various test equipment for endoscopes is described. For example, U.S. Pat. No. 6,203,492 and U.S. Pat. No. 6,673,011 describe pieces of equipment that hold and protect endoscopes when the pupil of the endoscopes are scanned for damage and debris. This equipment is easy to use but does not give a clear determination if the equipment is ready for use or not. The endoscope testing equipment described in U.S. Pat. Nos. 4,613,232, 5,966,210 and 6,498,642 use time consuming procedures to collect data that require technical knowledge and skills and checking of the data against a manufacturer's specification and tolerances. Further, U.S. Pat. No. 6,069,691 and U.S. Pat. No. 7,022,065 describe test equipment for endoscopes that is automated or computer controlled. This makes the equipment easier to handle, but the equipment is more expensive and delicate.

SUMMARY OF THE INVENTION

The present application is directed to test equipment for endoscopes which can be used by non technical staff in the hospital to determine if an endoscope is ready for use in surgery. The described equipment is used to determine the basic functionality of an endoscope prior to submitting it to the operating room. According to one aspect of the invention there is provided a rectangular mounting board attached to a base rail. On the base rail are two centering mounts holding the proximal end and distal end of an endoscope during testing. The centering mount holding the proximal end is mounted to one end of the base rail. The centering mount holding the distal end of the endoscope is integrated in a target holder sliding on the base rail to adjust the target holder to the length of the endoscope. Aside from the second centering mount, the target holder contains an adjustable positioning pin for the tip of the endoscope, and an optical test target which can be tilted and moved towards the tip of the endoscope. The test target has a resolution pattern in the center and resolution patterns distributed radially around the periphery of the test target. Attached to the base rail is a support rail on which an optical scanning device slides. This optical scanning device is mounted coaxially to the axis of the two centering mounts. By moving the optical scanning device along the endoscope axis, the exit pupil of the endoscope can be inspected. For visual inspection of the endoscope the inspection optics can be flipped away. The equipment further contains a microscope connected to the mounting board for inspection of the exterior of the endoscope, and a fiber visualization device which can be attached to the fiber illumination light post of the endoscope to inspect the fiber illumination bundle.

According to another aspect of the invention there is provided an endoscope testing apparatus including a base, a main rail coupled to the base, a first centering mount coupled to the main rail, an optical test target holder coupled to the main rail, a second centering mount coupled to the optical test holder, the second centering mount being coaxially alignable with the first centering mount, and an optical scanning device coupled to the main rail and coaxially alignable with the first centering mount and the second centering mount. Preferably, the first centering mount is immovably coupled to an upper end of the main rail and the test target holder is slidably coupled to the main rail. The test target holder includes a rotatable positioning pin and an optical test target coupled thereto and arranged to rotate about the positioning pin. The distance between the optical test target and the second centering mount is selectively adjustable as is the distance between the first centering mount and the second centering mount and the distance between the first centering mount and the optical scanning device. Preferably, the optical scanning device is slidably coupled to the main rail. A microscope can be coupled to the base if desired for inspecting the end surface of fiber illumination bundle of an endoscope.

According to another aspect of the invention there is provided a method of testing an endoscope. The method includes detachably coupling an endoscope to a base, coaxially aligning the endo scope between a first centering mount and a second centering mount coupled to an optical test holder, each of the first centering mount, the second centering mount and the optical test holder being supported by the base, coaxially aligning the endoscope between the first centering mount and an optical scanning device, the optical scanning device being supported by the base, and viewing an optical test target supported by the optical test holder through the endoscope. The method further includes adjusting the distance between the first centering mount and the second centering mount, the distance between the first centering mount and the optical scanning device, the distance between the second centering mount and the optical test target and an angle formed between an axis defined by the first centering mount and the second centering mount and the optical test target.

According to yet another aspect of the invention there is provided an endoscope testing apparatus including a first centering mount supported on a base and a second centering mount supported on the base and coaxially aligned with the first centering mount. The apparatus further includes an optical test target that is supported on the base and arranged to intersect an axis defined by the first centering mount and the second centering mount, the axis and optical test target forming a selectively adjustable angle. An optical scanning device is supported on the base and coaxially alignable with the first centering mount and the second centering mount. A first adjustable distance is defined between the first centering mount and the second centering mount. A second adjustable distance is defined between the second centering mount and the optical test target. Preferably, a main rail is coupled between the base and the first centering mount and the base and the second centering mount and the second centering mount and optical test target are slidably coupled to a main rail. It is also preferred that the main rail is coupled between the base and the first centering mount and the base and the optical scanning device and that a rotatable bracket is coupled between the main rail and the optical scanning device. In use, a proximal end of an endoscope is supported by the first centering mount and a distal end of the endoscope is supported by the second centering mount.

DETAILED DESCRIPTION OF PRESENTLY PREFERRED EMBODIMENTS

This invention relates to test equipment for rigid endoscopes, but also for flexible endoscopes and video endoscopes. The test equipment contains all necessary components to perform checks and tests on endoscopes necessary to verify the functionality of the endoscope. FIGS. 1 through 10 display an endoscope testing device 8 in accordance with a preferred embodiment of the present invention. Testing device 8 enables trained non-technical staff members in a hospital to perform simple functional tests and inspections of an endoscope 2 for determining whether endoscope 2 is ready for use in surgery or not. It can be used to do so without requiring data collection. Based on the findings of the tests, hospital staff can decide whether endoscope 2 is in a condition for operating room use. Inspection of endoscope 2 utilizing testing device 8 also enables hospital staff members to determine whether the functionality of tested endoscope 2 can be restored within the hospital by cleaning alone, for example, cleaning the outer surfaces of the endoscope lenses and illumination fiber bundle, or whether endoscope 2 requires cleaning or repair by trained personnel in a specialized facility.

Figure 1:
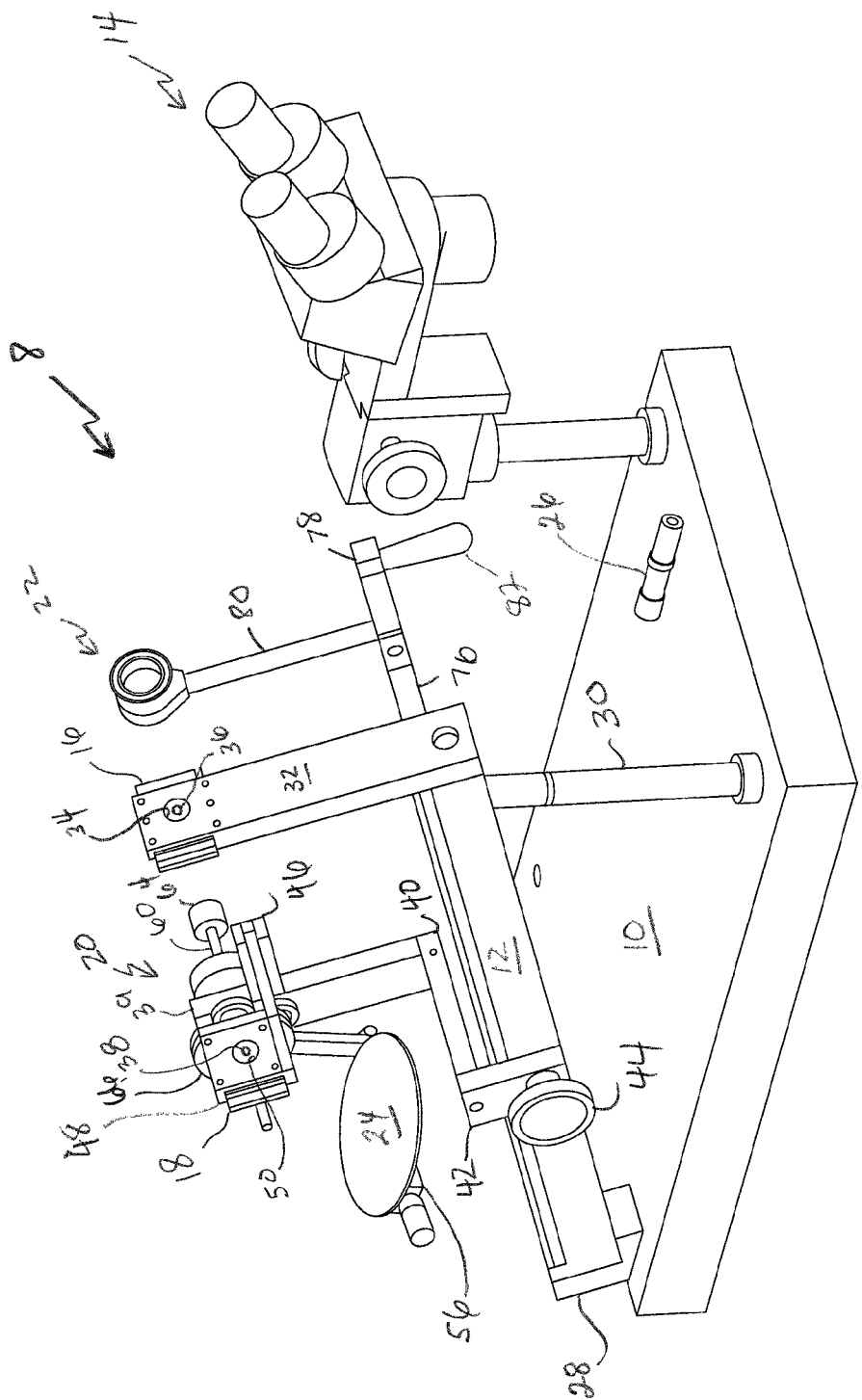
FIG. 1 is a perspective view of an endoscope testing device in accordance with a preferred embodiment of the present invention.

Referring to FIG. 1, testing device 8 generally includes a mounting board 10 for supporting a base rail 12 and an inspection microscope 14. Base rail 12, in turn, supports a first centering mount 16, a second centering mount 18, a test target holder 20 and an optical scanning device 22. In use, endoscope 2 is inserted through centering mounts 16 and 18 with a distal end 4 of endoscope 2 being directed toward an optical test target 24 supported by target holder 20. A user then examines test target 24 through scanning device 24 to check the optical performance of endoscope 2. Thereafter, the user can inspect the end surfaces of the fiber illumination bundle of endoscope 2 utilizing microscope 14 and a fiber visualization device 26 such as a fiber illuminator which has a reduced light out put to enable the visual inspection of the surface of the individual illumination fibers. All components of endoscope testing device 10, with the exception of fiber visualization device 26, are attached to mounting board 10 to avoid any component being lost.

More particularly, mounting board 10 is constructed from any hard, weighty material such as granite and provided as a rectangular prism-shaped thick piece base having a thickness of at least 2 centimeters. The straight edge of mounting board 10 is used to check the straightness of the outer tube of endoscope 2 and the alignment of the outer tube in reference to the body and eyepiece of endoscope 2. The straightness of the outer tube is checked by holding the outer tube of endoscope 2 against one side of rectangular mounting board 10 and turning the tube one full turn. A bent outer tube indicates that endoscope 2 may have experienced mechanical stresses that caused damage to or dislocation of the optical components inside of endoscope 2. Even if the outer tube is not bent along its length, the connection between the outer tube of endoscope 2 and the endoscope body can be bent. This is checked by pressing an axial surface of the endoscope body against one side of rectangular mounting board 10.

Rail 12 is connected to mounting board 10 at an angle with a lower end of rail 12 being coupled to board 10 via a first bracket 28 and an upper end of rail 12 being coupled thereto to by a first post 30. First centering mount 16 is supported on the upper end of base rail 12 by an elongate, first centering mount bracket 32 that is attached to the upper end of rail 12 with which it forms a right angle. Bracket 32 includes a slot extending laterally through the upper end thereof for receiving first centering mount 32 and a first opening 34 that is aligned with a first aperture 36 of first centering mount 16. First aperture 36 is centered within opening 34 and arranged to receive endoscope 2 and support the endoscope about a proximal end 6 thereof when in use.

Figure 2:
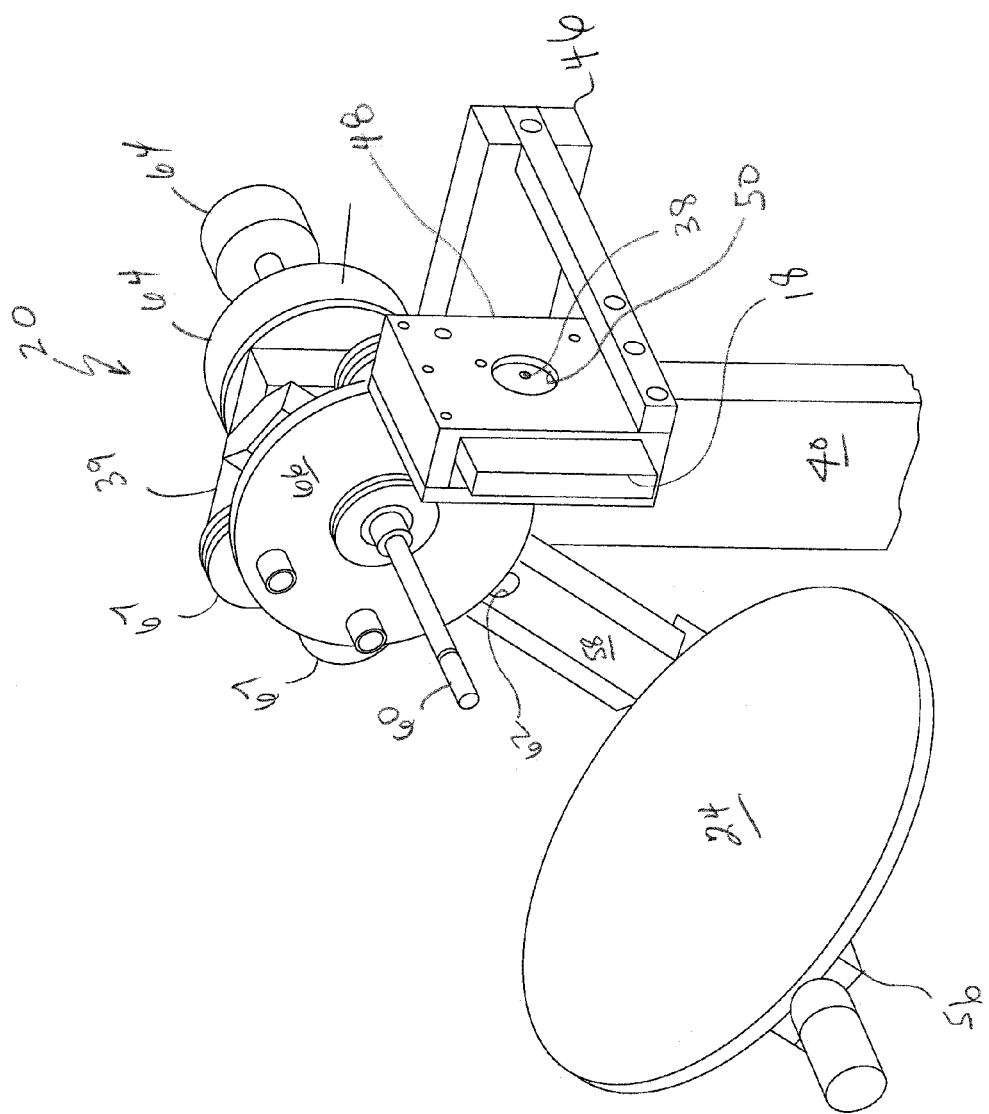
FIG. 2 is a perspective view of an optical test target holder of the endoscope testing device of FIG. 1.

First aperture 36 is coaxially aligned with a second aperture 38 that is formed through second centering mount 18. Referring to FIG. 2, second centering mount 18 is supported on a first L-shaped bracket 40 by a substantially horizontally arranged second L-shaped bracket 46 that is attached to an upper end portion 39 of bracket 40 and located opposite to first sliding bracket 42. A second centering mount bracket 48 is coupled to the free end of L-shaped bracket 46 and includes a second opening 50 coaxially aligned with first opening 34 of the first centering mount bracket 32. Second centering mount 18 is arranged to receive and support distal end 4 of endoscope 2. The distance between centering mounts 16, 18 can be adjusted by sliding second centering amount 38 along the length of base rail 12. In particular, second centering mount 18, along with test target holder 20 with which second centering mount 18 is integrated, are supported on a substantially vertically arranged first L-shaped bracket 40, that in turn, is coupled to base rail 12 by a first sliding bracket 42. Sliding bracket 42 includes a first knob 44 for securing bracket 42 to rail 12 by tightening the knob against the rail. Likewise, first knob 44 can be loosened thereby allowing first sliding bracket 42 to be moved along base rail 12 as desired. Accordingly, by moving first sliding bracket 40 along base rail 12, the distance between centering mounts 16, 18 can be adjusted. This way, test target holder 20 can be adjusted to the length of endoscope 2 and locked in position using first knob 44.

Figure 3:
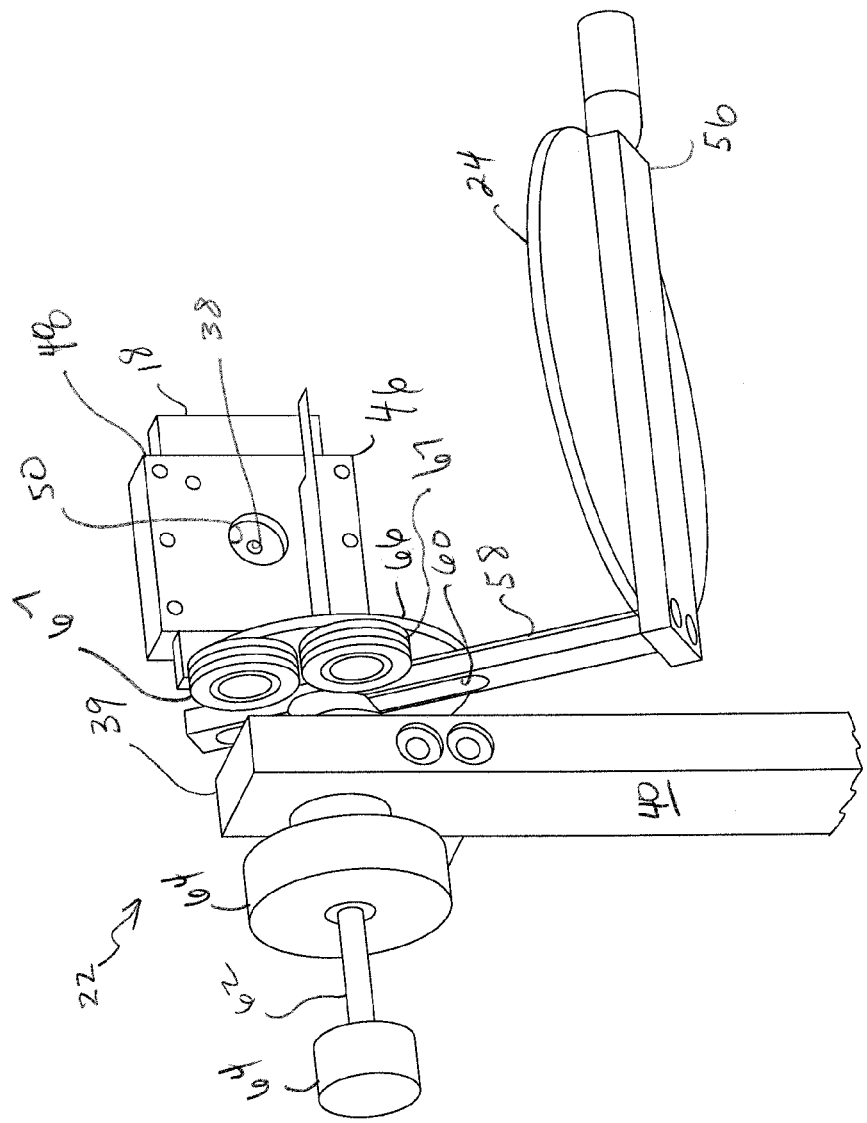
FIG. 3 is another perspective view of the optical test target holder of FIG. 2.
Figure 4:
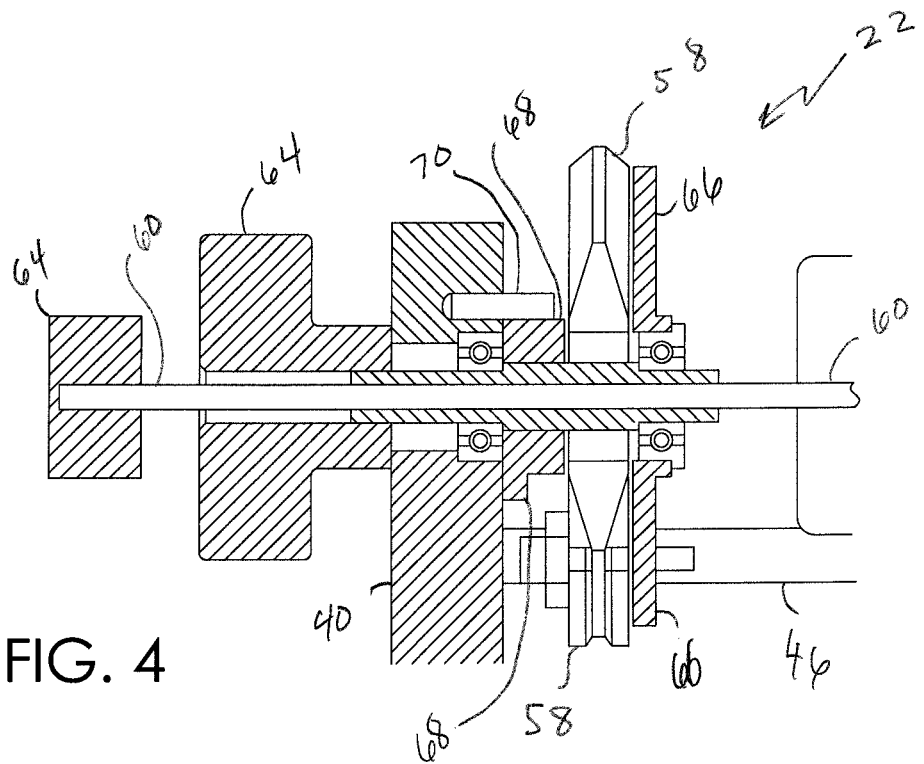
FIG. 4 is a sectional view of the optical test target of FIG. 2 through the positioning pin thereof in a locked position.
Figure 5:
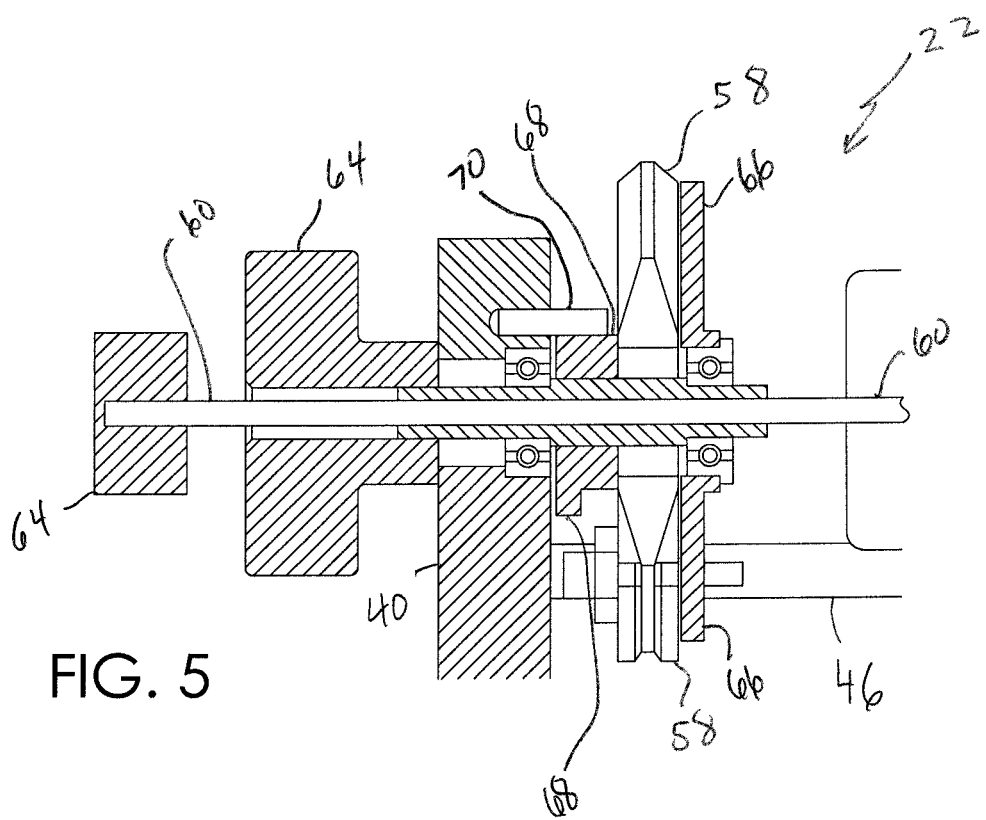
FIG. 5 is a sectional view of the optical test target of FIG. 2 through the positioning pin thereof in an unlocked position.
Figure 6:
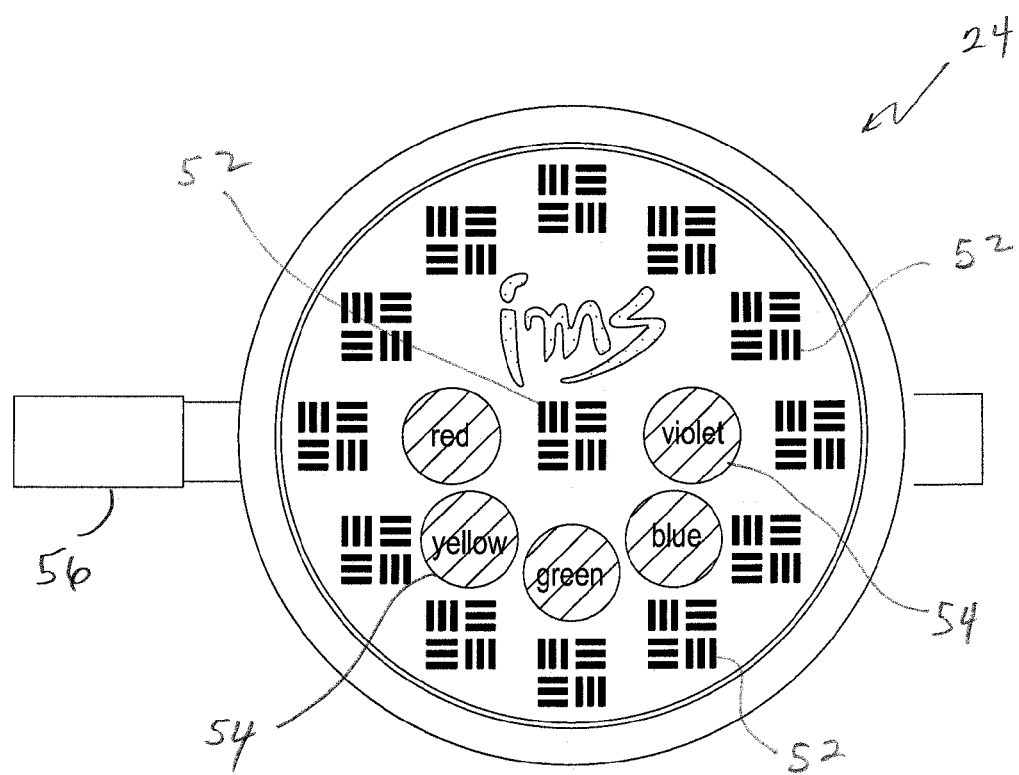
FIG. 6 is an elevational view of an optical test target of the optical test target holder of FIG. 2.

Alignable at selectively adjustable angles with the axis formed between first aperture 36 and second aperture 38 and at selectively adjustable distances from aperture 38 is optical test target 24 supported by test target holder 20. Test target 24 is arranged to tilt around an axis and slide along the optical axes of endoscope 2 to adapt to the field of view of endoscope 2. Referring to FIGS. 3 and 6, test target 26 is provided as a circular disc having a front surface with resolution patterns 52 distributed in the center and radially around the periphery of test target 24. Additionally, colored dots 54 are provided on the front surface for checking for any de-coloration of the imaging systems of endoscope 2. The adjustable angles and distances are accomplished by securing a back surface of test target 24 to a third L-shaped bracket 56 having an upper slotted arm 58 slideably coupled directly to upper end portion 39 of first L-shaped bracket 40 using a positioning pin 60 that extends through upper end portion 39 and a slot 62 in slotted arm 58. Pin 60 forms an axis about which third L-shaped bracket 56 and test target 24 can rotate. This way, test target 24 is alignable at selectively adjustable angles with the axis formed between apertures 36, 38 by selectively fixing third L-shaped bracket 56 to positioning pin 56 and rotating pin 60 using one of two second knobs 64 fixed to pin 60. Further, slot 62 has a length along which positioning pin 60 can travel thus allowing test target to be positioned closer to or farther from second centering mount 18.

More particularly, referring to FIGS. 2-5, third L-shaped bracket 56 is selectively fixed to upper end portion 39 of first L-shaped bracket 40 and positioning pin 60 utilizing a roller guide block 66, a blocking disk 68 and a guide pin 70. Specifically, positioning pin 60 with second knob 64 connected to one end of pin 60 and roller guide block 66 connected to the other end thereof extends through upper end portion 39 of first L-shaped bracket 40. Slotted arm 58 moves on roller guide block 66 between two pairs of rollers 67 with slot 62 moving over pin 60. Optical test target 24 is tilted around the rotational axis defined by positioning pin 60 to accommodate the angle of a deflection prism at distal end 4 of endoscope 2. The distance of optical test target 24 to distal end 4 of endoscope 2 is adjusted by sliding slotted arm 58 in roller guide block 66 forwards or backwards. Through the center of the rotational axis slides positioning pin 60 in and out to position distal end 4 of endoscope 2 relative to the center of the rotational axis. On a thread on the rotational axis sits blocking disk 68. Guide 70, which is connected to upper end portion 39 of first L-shaped bracket 40, forces blocking disk 68 to move towards slotted arm 58 and roller guide block 66 and lock them in angular and longitudinal position.

Figure 7:
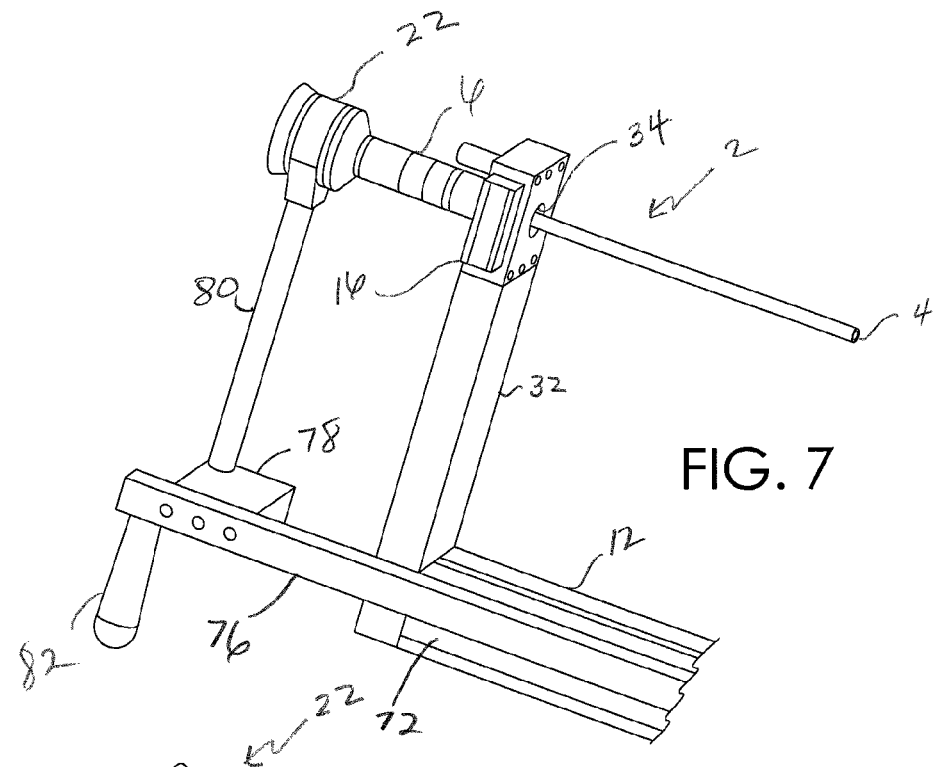
FIG. 7 is a perspective view of a centering mount and an optical scanning device assembly of the endoscope testing device of FIG. 1 operatively engaged in a first position with an endoscope.
Figure 8:
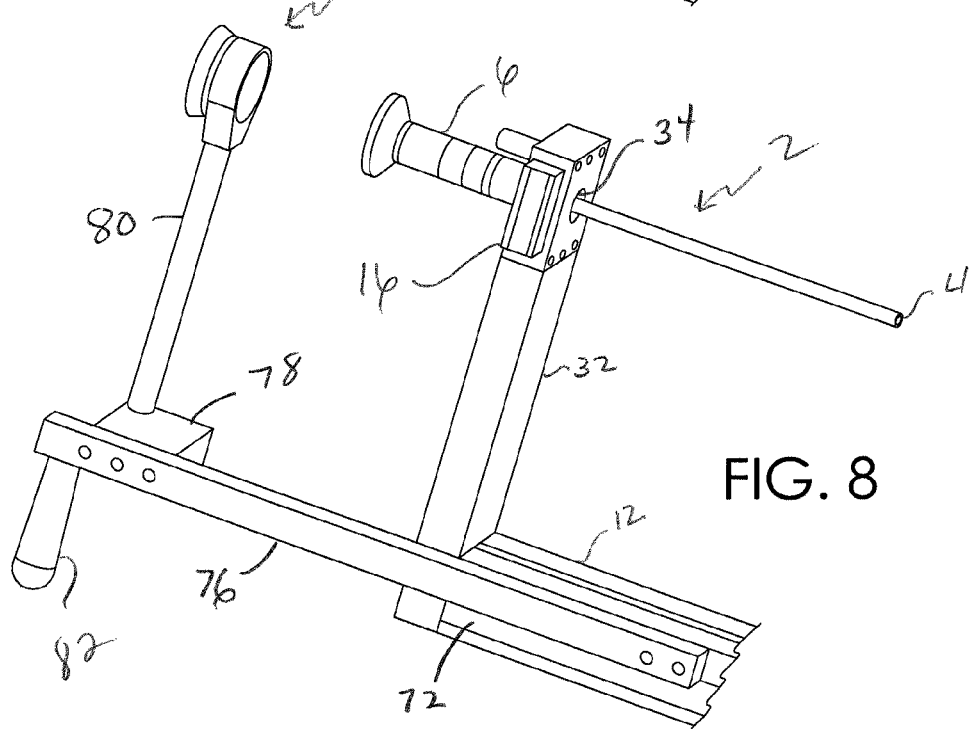
FIG. 8 is a perspective view of the optical scanning device assembly of FIG. 7 operatively engaged in a second position with the endoscope.
Figure 9:
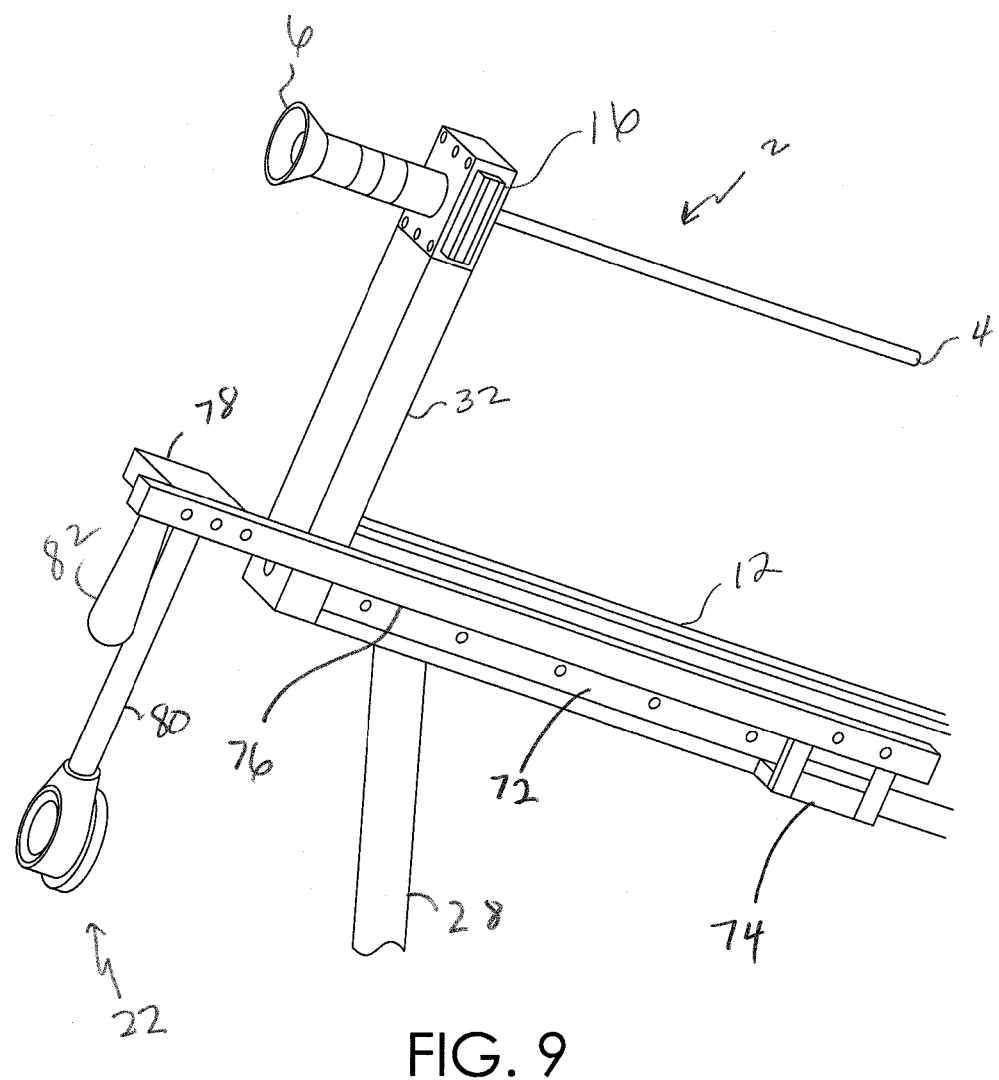
FIG. 9 is a perspective view of the optical scanning device assembly of FIG. 7 flipped away from the centering mount and disengaged from the endoscope.

Referring to FIGS. 7-9, attached to and along a length of base rail 12 opposite to first knob 44 is a support rail 72 on which a second sliding bracket 74 slides independently of first sliding bracket 42. Second sliding bracket 74 is connected to an extension arm 76 that can extend beyond a plane formed by first centering mount bracket 32 in a direction away from test target holder 20. A handle 82 is provided to assist with the extension of extension arm 76. A rotational bracket 78 is mounted to the free end of extension arm 76 and arranged to pivot around extension arm 76. Optical scanning device 22 is supported by rotational bracket 78 by an optics holder 80 which extends there between. Thus, on optics holder 80, optical scanning device 22 is mounted coaxially to the axis of the centering mounts 16, 18 and any endoscope 2 held therein. Optics holder 80 with optical scanning device 22 can be flipped off the axis of endoscope 2 through the rotational bracket 78. This way, optical scanning device 22 can be selectively coaxially aligned with the axis of centering mounts 16,18 sliding on support rail 72 mounted to base rail 12 and can be flipped out of alignment with the axis of centering mounts 16,18 during visual inspection of the image created by the optical system of endoscope 2. Thereafter, it can be flipped back in the position coaxially to the axis of centering mounts 16, 18 to inspect the pupil of the optical system of endo scope 2.

Figure 10:
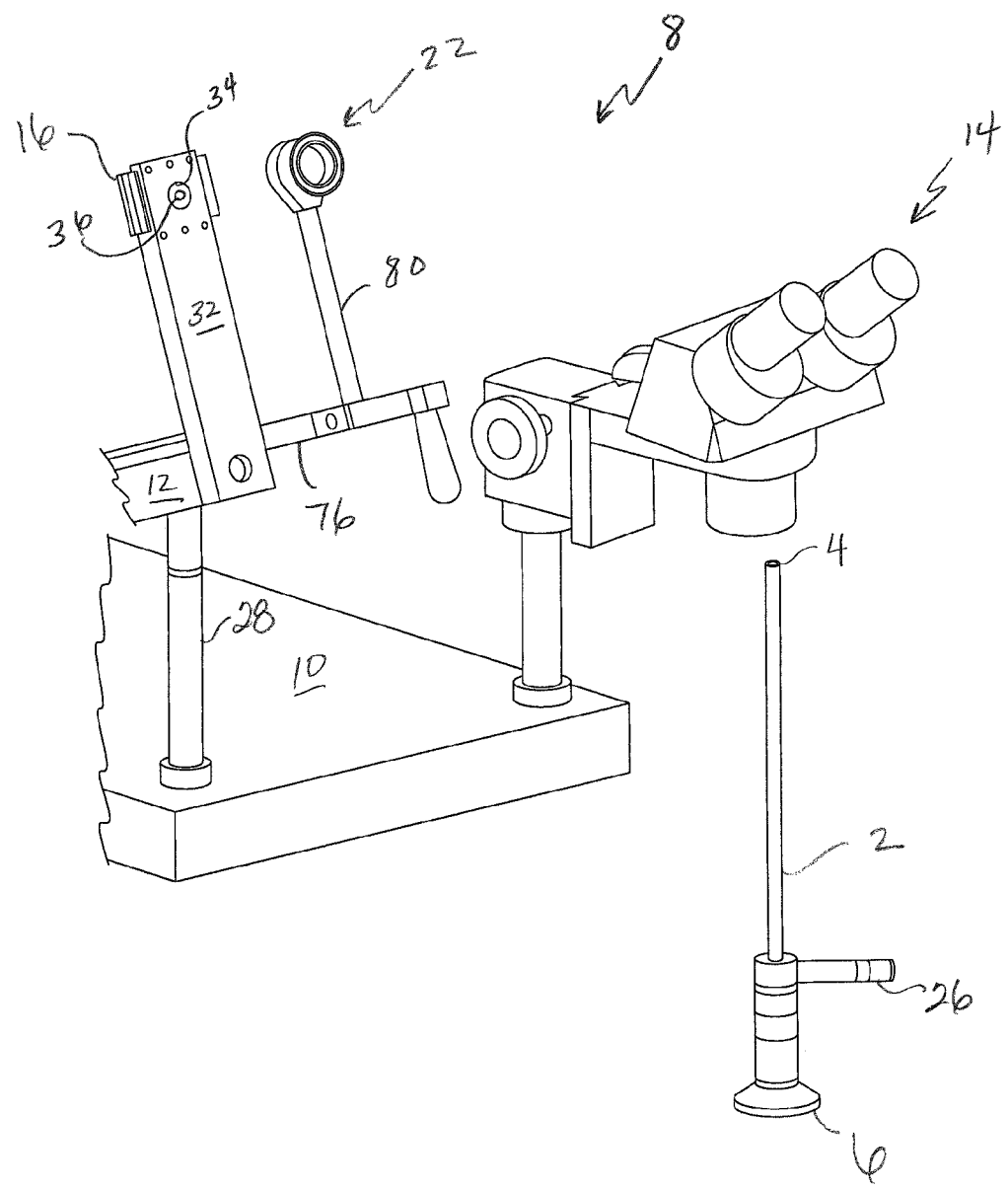
FIG. 10 is a perspective view of a microscope and fiber visualization device of the endoscope testing device of FIG. 1.

The tests to be performed utilizing test device 8 are used to analyze a set of physical and optical tests. In particular, after cleaning the outside surface of the windows on distal end 4 and proximal end 6 of the optical system of endoscope 2, the condition of the windows are examined under microscope 14. Sharp edges, cracks or visible internal fluid under the windows indicates a damaged distal end 4 of endoscope 2. After cleaning the entrance and exit surface of the fiber illumination bundle these surfaces are checked for any remaining debris. The illumination fibers built in endoscope 2 do not change the internal transmission or experience any color degradation over time. However some of the fibers can break or the fiber ends can be chipped or deposit on the fibers can reduce the light output so that endoscope 2 cannot transmit enough light to sufficiently illuminate the body cavity. When fiber visualization device 26 is attached to the fiber illumination bundle at the light post of endoscope 2 as illustrated in FIG. 10, the fiber bundle at distal end 4 can be visually checked for any broken or chipped fibers. Also any deposits reducing the light transmission on the fiber bundle end can be detected.

If none of these inspections indicates a damaged endoscope 2, the endoscope is placed in centering mounts 16, 18 with the distal end 4 facing optical test target 24 and touching positioning pin 60. While looking through the ocular of endoscope 2, test target 24 is tilted until the target is centered in the field of view of endoscope 2 and the distance between target and distal end 4 of endoscope 2 is adjusted so that the circular border of the test target fills the circular image field of endoscope 2. By comparing resolution pattern 52 of the center of the image field with the resolution patterns distributed around the periphery of test target 24 the image quality over the whole image field can be evaluated for endoscope 2. This is a functional test which indicates if the image of endoscope 2 delivers a sharp crisp image of an object positioned at an average working distance of the endoscope. If a fiber illumination light source is available or added as accessory to test device 8, the evenness of the illumination in the object field of endoscope 2 can also be evaluated by looking through the ocular of the endoscope.

After the optical system of endoscope 2 is evaluated, the clear aperture of the optical train of the endoscope is inspected. It is usual to scan the pupil area of optical systems to detect any dust, debris, fluid or damaged optical components. To inspect the pupil area over a certain depth range, endoscope 2 stays inside centering mounts 16, 18 and optical scanning device 22 is flipped in the coaxial position. Optical scanning device 22 with its inspection optics is moved along support rail 72 until it touches proximal end 6 of the eyepiece of the endoscope. While looking through optical scanning device 22, the optical scanning device is moved along support rail 72 away from the eyepiece of endoscope 2, and the pupil area of the endoscope is scanned for dust, debris, fluid or damaged optical components.

Optical scanning device 22 can be a simple loupe or magnifier to inspect the exit pupil of a rigid endoscope or the ocular of a flexible fiber endoscope, or the optical scanning device can be a telescope to inspect the fiber image bundle of a flexible endoscope through the ocular of the flexible endoscope. Video endoscopes which have the chip at the distal tip of the endoscope have no ocular at the proximal end. In this case the inspection lens stays flipped away from the coaxial position. Optical scanning device 22 and microscope 14 may each have an eyepiece meeting the standard of a medical endoscope so that any documentation camera adapted to the endoscope can also be adapted to the optical scanning device.

Optionally, test device 8 can be equipped with a commercially available endoscopic camera with a camera head and a camera controller and a monitor to display the endoscopic image. An additional fiber illumination light source can be also added to document the light distribution and image quality of endoscope 2. An additional image capturing or image recording device may be used to document the readiness and the degradation history of tested endoscopes. The camera can be connected for documentation and training purposes to the endoscope, optical scanning device 22 and microscope 14.

As will be apparent to one skilled in the art, various modifications can be made within the scope of the aforesaid description. Such modifications being within the ability of one skilled in the art form a part of the present invention and are embraced by the claims below.

It is claimed:

1. A method of testing an endoscope comprising,
providing a base supporting a first centering mount and a second centering mount,
coaxially aligning the endoscope between the first centering mount which supports a proximal end of the endoscope and the second centering mount which supports a distal end of the endoscope, wherein the second centering mount is coupled to an optical test holder, the second centering mount and the optical test holder forming a unit,
slidably supporting the unit and the first centering mount on a rail,
moving the unit relative to the first centering mount,
adjusting the distance between the second centering mount and the optical test target,
coaxially aligning the endoscope with an optical scanning device, the optical scanning device being supported by the rail about the proximal end of the endoscope and movable relative to the first centering mount, and
viewing an optical test target supported by the optical test holder through the endoscope.

2. The method according to claim 1 comprising adjusting the distance between the first centering mount and the second centering mount.

3. The method according to claim 1 comprising adjusting the distance between the proximal end of the endoscope and the optical scanning device.

4. The method according to claim 1 comprising adjusting the distance between the second centering mount and the optical test target without adjusting the distance between the second centering mount and the first centering mount.

5. The method according to claim 1 comprising adjusting an angle formed between an axis defined by the endoscope and the optical test target.

6. The method according to claim 5, wherein the angle formed between the axis defined by the endoscope and the optical test target is adjusted by tilting the optical test target about a horizontal axis.

7. The method according to claim 5, wherein the angle formed between the axis defined by the endoscope and the optical test target is adjusted by tilting the optical test target about a pin supported by the optical test holder.

8. The method according to claim 1 comprising pivoting the optical scanning device out of coaxial alignment with the endoscope.

9. The method according to claim 1 comprising arranging the rail at an angle to a top surface of the base with a proximal end of the rail being provided at a greater distance above the top surface than a distal end of the rail.

10. The method according to claim 1 comprising inspecting the endoscope with a microscope that is coupled to the base.

11. The method according to claim 1 further comprising arranging a first axis defined by the endoscope to intersect a second axis about which the optical test target is rotatable.

12. A method of testing an endoscope comprising,
providing a base having a rail, the rail supporting a first support mount, a second support mount, an optical test holder and an optical test target supported by the optical test holder,
arranging a proximal end of an endoscope on the first support mount and a distal end of the endoscope on the second support mount with a first axis defined by the endoscope intersecting the optical test target,
moving the second support mount and the optical test holder as a single unit along the rail,
tilting the optical test target about a second axis,
viewing the optical test target through the endoscope,
wherein the optical test target includes a plurality of resolution patterns.

13. The method according to claim 12 further comprising moving the second support mount and the optical test holder as a single unit relative to the first support mount.

14. The method according to claim 12 further comprising moving the second support mount and the optical test holder linearly as a single unit relative to the first support mount.

15. The method according to claim 12 further comprising providing the optical test target with a surface displaying the plurality of resolution patterns, a first colored portion, and a second colored portion that is a different color from the first colored portion and viewing the plurality of resolution patterns, the first colored portion, and the second colored portion through the endoscope.

16. The method according to claim 12 wherein the second axis extends horizontally.

17. The method according to claim 12 wherein the first axis intersects the second axis.

18. The method according to claim 12 comprising adjusting the distance between the first support mount and the second support mount by sliding the second support mount along the rail supported by the base.

19. The method according to claim 12 comprising inspecting a proximal end of the endoscope with an optical scanning device while the endoscope is supported by and between the first support mount and the second support mount.

20. The method according to claim 12 comprising adjusting the distance between the second support mount and the optical test target.

21. A method of testing an endoscope comprising,
providing a base having a rail, the rail supporting a first support mount, a second support mount, an optical test holder and an optical test target supported by the optical test holder,
arranging a proximal end of an endoscope on the first support mount and a distal end of the endoscope on the second support mount with a first axis defined by the endoscope intersecting the optical test target,
moving the second support mount and the optical test target holder as a single unit along the rail, wherein moving the unit alters a distance between the unit and the first support mount,
tilting the optical test target,
viewing the optical test target through the endoscope.

22. The method according to claim 21 further comprising viewing a plurality of resolution patterns on a surface of the optical test target.

23. The method according to claim 22 further comprising viewing a first colored area and a second colored area on the surface of the optical test target, the first colored area including a color not found in the second colored area.

24. The method according to claim 21 further comprising moving the second support mount and the optical test holder as a single unit along the rail supported by the base.

25. The method according to claim 21 further comprising moving the second support mount and the optical test holder linearly as a single unit relative to the first support mount.

26. The method according to claim 21 wherein the optical test target is tilted about a horizontally extending axis.

27. The method according to claim 26 wherein the first axis intersects the horizontally extending axis.

28. The method according to claim 21 comprising adjusting the distance between the first support mount and the second support mount by sliding the second support mount along the rail supported by the base.

29. The method according to claim 21 comprising inspecting a proximal end of the endoscope with an optical scanning device while the endoscope is supported by and between the first support mount and the second support mount, the second support mount and the optical scanning device being slidably supported by the rail supported by the base.

30. The method according to claim 21 comprising adjusting the distance between the second support mount and the optical test target.

* * * * *